(12) United States Patent
Sevy (10) Patent No.: US 11,065,358 B2
(45) Date of Patent: Jul. 20, 2021

(54) AIR-BLADE, SILENCER AND SEPARATOR APPARATUS AND METHOD

(71) Applicant: Earl Vaughn Sevy, Cedar City, UT (US)

(72) Inventor: Earl Vaughn Sevy, Cedar City, UT (US)

(*) Notice: Subject to any disclaimer, the term of this patent is extended or adjusted under 35 U.S.C. 154(b) by 489 days.

(21) Appl. No.: 15/689,763

(22) Filed: Aug. 29, 2017

(65) Prior Publication Data

US 2017/0354753 A1 Dec. 14, 2017

Related U.S. Application Data

(63) Continuation-in-part of application No. 29/554,486, filed on Feb. 11, 2016, now Pat. No. Des. 811,576.

(Continued)

(51) Int. Cl.
| | | |
|---|---|---|
| *A61L 9/14* | (2006.01) | |
| *B05B 1/26* | (2006.01) | |
| *B05B 7/00* | (2006.01) | |
| *B05B 7/24* | (2006.01) | |
| *B05B 1/00* | (2006.01) | |
| *B05B 14/00* | (2018.01) | |

(52) U.S. Cl.
CPC ............... *A61L 9/14* (2013.01); *B05B 1/002* (2018.08); *B05B 1/262* (2013.01); *B05B 7/0012* (2013.01); *B05B 14/00* (2018.02); *B05B 7/2424* (2013.01)

(58) Field of Classification Search
CPC .......... A61L 2209/13; A61L 2209/11; A61L 2209/14; A61L 9/205; A61L 9/14; B05B 1/26; B05B 1/262; B05B 7/005; B05B 7/0425; B05B 7/2405; B05B 1/002; B05B 1/005; B05B 1/02; B05B 14/00; B05B 14/10
USPC ........................................................ 239/338
See application file for complete search history.

(56) References Cited

U.S. PATENT DOCUMENTS 904,149 A 11/1908 Rachmann
2,826,454 A 3/1958 Coanda
(Continued)

FOREIGN PATENT DOCUMENTS

JP 2001046920 9/2002

OTHER PUBLICATIONS

Tetra Whisper Aquarium Air Pump 300, Aquarium Guys, Oct. 8, 2008 p. 1, http://www.aquariumguys.com/tetraairpump4.html.
(Continued)

*Primary Examiner* — Qingzhang Zhou
*Assistant Examiner* — Christopher R Dandridge
(74) *Attorney, Agent, or Firm* — Pate Baird, PLLC (57) ABSTRACT

Silencing and separation in a cold-air, essential-oil, diffuser apparatus and method pass flow through a channel having comparatively high aspect ratios of length to thickness and width to thickness. Curved, tapered, non-parallel, and quasi random surfaces reduce probability and power of resonant frequencies. Offsetting flow through a channel is followed by impingement against an obstructing surface, redirection elsewhere within a drift (separation) chamber, and exiting through a smaller, and differently oriented exit port. Silencing is improved by changes of cross-sectional area creating high-pass and low pass acoustic filters, changes of direction, and absorption of acoustic energy in fluid-droplet-laden air.

19 Claims, 7 Drawing Sheets

Section A-A

Related U.S. Application Data (60) Provisional application No. 62/459,013, filed on Feb. 14, 2017.

(56) References Cited

U.S. PATENT DOCUMENTS

| | | | |
|---|---|---|---|
| 3,112,074 | A | 11/1963 | Green |
| 3,515,966 | A | 6/1970 | De Valroger et al. |
| 3,641,757 | A | 2/1972 | Rehn |
| 4,235,611 | A | 11/1980 | Brownell |
| 4,243,396 | A | 1/1981 | Cronenberg |
| 4,976,259 | A | 12/1990 | Higson et al. |
| 5,029,759 | A | 7/1991 | Weber |
| 5,054,477 | A | 10/1991 | Terada et al. |
| 5,137,432 | A | 8/1992 | Tsai |
| 5,201,641 | A | 4/1993 | Richer |
| 5,248,448 | A | 9/1993 | Waldron et al. |
| 5,309,900 | A | 5/1994 | Knoch et al. |
| 5,314,529 | A | 5/1994 | Tilton et al. |
| 5,409,170 | A * | 4/1995 | Burwell ............... B05B 7/0012 128/200.18 |
| 5,549,247 | A | 8/1996 | Rossman et al. |
| 5,579,758 | A | 12/1996 | Century |
| 5,687,710 | A | 11/1997 | Ambrosio et al. |
| 5,875,774 | A | 3/1999 | Clementi et al. |
| 5,922,247 | A | 7/1999 | Shoham et al. |
| 6,029,913 | A | 2/2000 | Stroia et al. |
| 6,168,392 | B1 | 1/2001 | Takano |
| 6,217,281 | B1 | 4/2001 | Jeng et al. |
| 6,236,042 | B1 | 5/2001 | Kato et al. |
| 6,364,637 | B1 | 4/2002 | Hase et al. |
| 6,669,176 | B2 | 12/2003 | Rock |
| D491,259 | S | 6/2004 | Garrison et al. |
| D491,258 | S | 7/2004 | Sevy |
| D492,020 | S | 7/2004 | Sevy |
| D509,893 | S | 9/2005 | Sevy |
| 6,968,069 | B1 | 11/2005 | Zhao |
| D520,129 | S | 5/2006 | Sevy |
| D526,710 | S | 7/2006 | Sevy |
| 7,407,118 | B2 | 8/2008 | Sevy |
| 7,712,683 | B2 | 5/2010 | Robert et al. |
| 7,878,418 | B2 * | 2/2011 | Sevy ............... A61M 11/06 128/200.18 |
| 7,930,068 | B2 | 4/2011 | Robert et al. |
| 8,001,963 | B2 | 8/2011 | Giroux |
| 9,126,215 | B1 * | 9/2015 | Levy ............... B05B 14/00 |
| 9,415,130 | B2 | 8/2016 | Sevy |
| 2008/0283049 | A1 | 11/2008 | Mahoney et al. |
| 2013/0327323 | A1 | 12/2013 | Rubin |
| 2014/0294667 | A1 * | 10/2014 | Sevy ............... A61L 9/14 422/4 |

OTHER PUBLICATIONS

Optima Air Pump A807, Aquarium Guys, Oct. 8, 2008, p. 1, http://www.aquariumguys.com/optimaairpump.html.

Silent Air X-4 Air Pump, Aquarium Guys, Oct. 8, 2008, p. 1, http://www.aquariumguys.com/silentairpump4.html.

Whisper 60 Aquarium Air Pump, Aquarium Guys, Oct. 8, 2008, p. 1, http://www.aquariumguys.com/tetra-whisper60-air-pump.html.

Rena Air 400 Air Pump 702E, Aquarium Guys, Oct. 8, 2008, p. 1, http://www.aquariumguys.com/renaairpump4.html.

Tom Stellar Air Pumps S-30, Fish Tanks Direct, Oct. 8, 2008, p. 1, http://www.fishtanksdirect.com/index.asp?PageAction=VIEWPROD&ProdID=2102.

Aroma-Globe™ Essential Oil Diffuser/Nebulizer Diffuser World, Oct. 8, 2008, p. 1 http://www.diffuserworld.com/aromaglobATM-essential-oil-diffusernebulizer-p-10.html.

Nebulizing Diffuser, Betterherbs, Oct. 8, 2008, http://betterherbs.serrahost.com/Detail.bok?no=397.

Auroma Nebulizer for the House, Shop.com, Oct. 8, 2008, p. 1 http://www.shop.com/Auroma_Nebulizer_for_the_House_diffuser-46805905-p!.shtml.

Aura Cacia Electric Diffuser House Model, Shop.com, Oct. 8, 2008, p. 1, http://www.shop.com/Aura_Cacia_Electric_Diffuser_House_Model_diffuser-46805768-p!.shtml.

Essential Air Room Diffusers, Leyden House, Oct. 8, 2008, p. 1 http://www.leydenhouse.com/diffuers.html.

http://www.air-aroma.com/diffusers, Mar. 21, 2013.

http://www.prolitec.com/appliances_commercial.htm, Mar. 21, 2013.

http://scentair.com/why-scentair-solutions/, Mar. 21, 2013.

http://www.brandaroma.com/products/, Mar. 21, 2013.

http://www.e2aroma.com/appliances/smart-air-maxi/, Mar. 21, 2013.

http://www.scentaustralia.com.au/index.php/products/scent-diffuser-zephyr, Mar. 21, 2013.

http://www.voitair.com/scent-systems, Mar. 21, 2013.

http://www.fragrancemachine.com/, Mar. 21, 2013.

Spa Room Purilizer Assortment with instructions, http://www.sparoom.com/catalog/, webpage, Sep. 1, 2015.

Floracopeia, Inc., S3 Nebulizing Diffuser, User Manual Apr. 2015.

Shenzhen Jing Xin, Sharing Together Pure Aromatic Fresh Air Catalog, Apr. 2015.

\* cited by examiner

Section A-A

AIR-BLADE, SILENCER AND SEPARATOR APPARATUS AND METHOD

RELATED APPLICATIONS

This application claims the benefit of U.S. Provisional Patent Application Ser. No. 62/459,013, filed Feb. 14, 2017, and is a continuation-in-part Application of U.S. patent application Ser. No. 29/554,486, filed Feb. 11, 2016, both of which are hereby incorporated herein by reference. This application incorporates by reference: U.S. patent application Ser. No. 12/247,755, filed Oct. 8, 2008, issued Feb. 1, 2011, as U.S. Pat. No. 7,878,418; U.S. patent application Ser. No. 13/854,545, filed Apr. 1, 2013; U.S. patent application Ser. No. 14/260,520, filed Apr. 24, 2014; U.S. Provisional Patent Application Ser. No. 62/265,820, filed Dec. 10, 2015; U.S. patent application Ser. No. 14/850,789, filed Sep. 10, 2015; and U.S. Provisional Patent Application Ser. No. 62/277,343, filed Jan. 11, 2016.

BACKGROUND

Field of the Invention

This invention relates to atomization of liquids and, more particularly, to novel systems and methods for separating larger droplets from smaller droplets in cold air diffusers of essential oils and other aromatic materials.

Background Art

Mechanisms exist for altering a closed environment such as a room or home with humidity. Likewise, mechanisms exist for removing humidity. Electronic and chemical mechanisms for destroying microbial sources of undesirable scents exist. Meanwhile, sprays, evaporators, wicks, candles, and so forth also exist to distribute volatile scents, essential oils, liquids bearing scents, and so forth. These may be introduced into breathing air, an atmosphere of a room, or any other enclosed space.

Heating often destroys or at least changes the constitution of essential oils. Thus, it has limitations. However, the evaporation rates or atomization rates of essential oils are often insufficient to provide a controllable, sustainable, and sufficient amount of an essential oil into the atmosphere. Thus, wicks having no air movement mechanism often prove inadequate.

Meanwhile, mechanisms that seek to copy vaporizers and moisture atomizers often damage surrounding equipment, furniture, and other environs of a space being treated by essential oils. Moreover, the continuing "spitting" by atomizers of comparatively larger droplets not only causes damage to finishes on surrounding surfaces, but wastes a substantial fraction of the essential oil.

Essential oils are concentrated sources of aromas or scents. Their extraction from source plants is sometimes complicated and comparatively expensive, based on the cost per unit volume of the essential oil. Therefore, colognes, other fragrance distribution systems, and the like often use high rates or fractions of diluents for essential oils. They may also use synthetic oils, water, and artificial scents that may dilute and not replicate the comforting, familiar, and natural essence of pure, essential oils.

By whatever mode, systems to distribute essential oils often waste an expensive commodity while damaging surroundings about their atomizers or other distribution systems. Thus, it would be an advance in the art to provide an apparatus and method for distributing essential oils in as small particles as possible, preferably vaporized, but having a size sufficiently small that air drag forces sustain them by dominating gravity forces tending to drift them out of the air. Thus diffusion efficiency needs to increase, while protecting surrounding areas. It would be an advance to do so while retrieving and recycling for re-atomization or diffusion droplets that are larger than those that may be sustained by air motion to remain airborne once discharged into surrounding air.

It would be a further advance in the art to quiet a diffuser. The chatter of reciprocating pumps is annoying. The hiss of atomizers spraying air and entraining droplets therein often transmits into a room at highly audible levels.

It would also be an advance in the art to improve separators and silencers to make them smaller, more compact, and more mobile, so they may be used with any source of air or atomizer. It would help to find a system suitable for a room, or even carried in a vehicle. Adding aromas to vehicles has long been the purview of poorly constructed and short-lived, absorbent materials filled with an oil and suspended by a tether from a mount of a rear view mirror. Effective selection of scent, duration and intensity of scent, and other desirable controls have been effectively absent. Moreover, the complexities of atomizers, separators, and silencers sizes, ineffectiveness, and have likewise been a deterrent to rapid and simplified mechanisms for diffusing essential oils and other liquids.

It would be an advance in the art to provide an integrated, universal separator and silencer. Simplifying and integrating are serious challenges. Controlling do not appear to be understood or applied. It would be a substantial benefit to a user to have a system tested and applying operational characteristics effective to a separate and silence in a compact user.

BRIEF SUMMARY OF THE INVENTION

In view of the foregoing, in accordance with the invention as embodied and broadly described herein, a method and apparatus are disclosed in one embodiment of the present invention as including a separator system that operates as a silencer and as a droplet separator for removing comparatively larger droplets and leaving comparatively smaller droplets entrained in a flow of air.

In certain embodiments, the overall system involves a reservoir operably connected by a line or tube drawing liquid from a reservoir into an atomizer. The atomizer may include a venturi as that word is understood in engineering.

A venturi is a condition defining a throat with a decreasing cross-sectional area of flow moving toward a central or middle portion followed by an increasing cross sectional area in a subsequent trailing portion. At the narrowest part of the throat, a port or opening in the wall of the conduit permits a second material to enter into the flow through the venturi. The constant value of dynamic head constituted by pressure head and velocity head results in a reduced static pressure near the midway point of the throat. This reduced static pressure draws material into the flow from the open port. A conventional carburetor operates on this principle.

In other embodiments, the atomizer may rely on an eductor. An eductor is a different mechanism mechanically, aerodynamically, and hydrodynamically. For example, an eductor relies on direct momentum transfer between an incoming jet and a surrounding fluid. By direct contact between the material in the jet with the surrounding material, the surrounding material receives momentum from the jet 
and thereby accelerates, joining and broadening the jet, necessarily slowing it. The acceleration of the surrounding material results in it being drawn away from its original location, creating a draw bringing replacement material in. Thus, an eductor operates as a pump in which a comparatively high speed jet induces the flow of a comparatively low speed or even stationary surrounding fluid. Thus the size of the jet and its total mass increase as its speed slows.

The eductor portion of the atomizer educts into a flow of air a liquid drawn through the tube from the reservoir. The liquid is atomized by the vigorous flow of the air jet that causes the eduction, resulting in a Gaussian distribution of liquid droplets.

The liquid droplets entrained in the airflow are cast into a first separation chamber or drift chamber in which they will eventually be required to change direction. Typically, the educted flow will impact or strike a wall opposite its nozzle that discharges the jets, resulting in a certain amount of adhesion and coalescence by comparatively larger droplets, a change of direction of the airflow, with a consequent change of direction of the comparatively smaller droplets remaining entrained in the airflow.

Larger droplets that coalesce against a wall drip down out of the separation chamber or drift chamber toward the reservoir. Droplets sufficiently small to remain entrained within the airflow change direction, move away from the wall and eventually move toward an exit.

In certain embodiments, a silencer or air-blade silencer may be a portion of or may penetrate through a separator plate separating the first or initial drift chamber or separation chamber from a subsequent or second such chamber. In fact, the air blade itself may be a comparatively long, wide, and thin channel. By thin is meant that the comparative thickness of the flow channel, compared to the width thereof, and compared to the longitudinal length measured along the direction of flow through that channel is comparatively small. The width and the length may have an aspect ratio (relationship, ratio) of about one. On the other hand, the aspect ratio of thickness to length or thickness to width, may be less than 0.5, and typically 0.2, 0.1, or less.

In operation, the air blade channel effectively sets up a boundary layer flow near the walls. As a result, the central core of flow through the air blade channel sets up a flow regime as known in fluid mechanics in which velocity of air along the central axis along the flow path in the air blade travels at maximum velocity and the velocity of air at the walls is effectively zero.

Thus, a velocity profile is established as described in any text on fluid mechanics. Therefore, droplets are being shed as the flow slows toward the outside walls, larger droplets being coalesced against the walls upon contact. Comparatively smaller droplets capable of remaining in the airflow continue onward through the channel on a trajectory virtually identical to that of the air. Thus, one may see that the air blade operates as a separator channel.

The air blade feeds into a second drift chamber. The second drift chamber operates similarly to the first. Here, the flow through the air blade channel is directed vertically toward a fixed, horizontal wall in the nature of a lid or cap over the second drift chamber. Thus, flow from the air blade is directed to strike the lid, and change direction. Again, impact against the lid or cap results in separation (by shattering, coalescing, or a combination) of comparatively larger droplets. Likewise, comparatively smaller droplets capable of remaining entrained with the airflow stay with it, and are directed or shunted away from actual impact with the lid, remaining with the airflow. For the sake of completeness, it should be understood that entrainment is a term of art, used in it engineering sense as defined in fluid mechanics. It is the mutual engagement of fluid particles, resulting from fluid drag and momentum transfer therebetween. Ultimately, flows of air with their entrained, "comparatively smaller" droplets pass through the second drift chamber and eventually find their way to an exit port.

The exit port is intentionally offset so as not to align with the air blade. That is, for example, flow from the air blade (the think airflow from a separator tower) cannot pass directly toward and out of the port, without a change of direction. Typically, the port is set eccentrically, off center, with respect to the lid, and is registered 180 degrees out of phase with the air blade. Thus, the air blade discharges from its tower as a thin flow of air containing atomized droplets, to impinge against a solid portion of the lid, from whence the airflow must change direction. It must flow through the second drift chamber, and ultimately change direction to again move vertically out through the exit port.

The offset of the exit port has been found to be extremely important from both a separation view point (separating comparatively larger droplets out from the flow) as well as a silencing perspective (reducing the decibels of noise audible outside the system) during operation. Thus, the air blade silencer system includes and operates as a channel separator or air blade separator and a drift chamber separator. In addition, the air blade silencer system operates as a noise reduction system removing significant noise, otherwise vert audible, originating with operation of the system in accordance with the invention.

A separator plate in certain embodiments of an apparatus in accordance with the invention may operate similar to a separator plate in other systems described in the references incorporated hereinabove by reference. For example, separator plates having a single aperture, multiple apertures, apertures near the center, apertures near the edges, and so forth have been disclosed in those documents. However, the small aspect ratio of thickness to width and small aspect ratio of thickness to length are new, unique to certain of the latest inventions of Applicant.

Here, the separator plate is penetrated by a thin channel, through a tower, that effectively travels vertically. In other embodiments, the channel has traveled circumferentially in a spiral. In others, an annular channel carried the flow, and operated as a separator based on aerodynamic and hydrodynamic principles.

Here, the channel is not permitted to be fully annular, in order to provide the offset of the air blade from the outlet port. This results in a reduction in sound of from about six to about 10 decibels. Typically, the hiss of the atomizer is silenced by about eight decibels in sound amplitude.

Moreover, the offset results in two drift chambers and an air blade channel (in the tower) all acting as separators. Thus, three separation processes occur resulting in virtually no "spitting" of comparatively larger droplets. By comparatively larger droplets is meant those that will not sustain themselves indefinitely in a flow of air. That is, they are sufficiently large in diameter and cross sectional area that their mass becomes sufficiently large to overcome (e.g., dominate) the aerodynamic drag thereon in a flow of air.

Comparatively large droplets tend to drift out of an airstream landing on furniture, floors, counters, carpets, bedding, and the like in the vicinity of a diffuser. Thus, it has been found that offsetting the air blade from the outlet port by from about 90 to about 180 degrees provides a reduction ad apparently entire elimination of substantially all comparatively larger liquid droplets.

Meanwhile, an optimum reduction in sound results with about a 180 degree rotation out of phase between the outlet port and the center of air blade (center line of flow).

In one embodiment, the air blade separator and silencer may have a neck fitted to an atomizer to receive flows therefrom. The neck may be fitted by a collar having a reduced or increased cross sectional area in order to pilot radially and register in a circumferential direction with the atomizer.

In certain embodiments, the outer wall of the air blade channel (and tower) may actually be coincident with the wall of the neck. Meanwhile, an inner wall of the tower defining the air blade channel may be shaped to provide a drip edge for coalesced droplets that have returned to a consolidated liquid and dripped down the inner wall of the tower defining the air blade channel. Thus, a lower edge of the inner wall of the air blade channel may be angled to promote droplets collecting thereon to drift to a lowest point thereon. That angle toward the lowest point or drip point encourages collection along the drip edge with resulting coalescence and dropping from the drip point. Thus, if an individual separates the silencer or separator from the atomizer, most residual oil does not remain.

Meanwhile, a drain or exit port for coalesced liquids within the bowl of the silencer or separator may be favored by a canting or tilting angle of the separation plate that operates as the bottom or floor of the bowl. In this way, any coalesced droplets within the bowl drip down to the separator plate, which then passes them along its angled surface toward the exit or drain.

In certain embodiments, the neck of the silencer may register at a specific point with the atomizer. For example, in one currently contemplated embodiment, the air blade is registered to be positioned opposite the inlet for the eductor.

Due to the vigor of the flow through the eductor, and the right-angle relationship between the direction of the central axis of the flow (jet) out of the eductor compared to the flow direction of the air blade, there is virtually no probability that the largest of the comparatively larger droplets will be passed through the air blade from the initial separation chamber or directly from the educted flow. Thus, flow from the eductor progresses toward an opposite wall, where comparatively larger droplets strike the wall of the first drift chamber. They may be shattered, coalesced, both, or otherwise altered.

Meanwhile, comparatively smaller droplets that remain with the airflow may drift around the drift chamber, eventually finding their way with the airflow into the air blade. Comparatively larger droplets initially with the airflow through this tortuous path are relegated to strike a wall and coalesce, eventually to drip back into the reservoir. The cap of the silencer is registered with the bowl in order to provide an offset of 180 degrees between the center of the air blade and the outlet port from the silencer or separator.

In order to minimize capillary action, a capillary break may be provided as a channel containing air and encircling substantially the entire circumference of the cap. Thus, no capillary path exists from within the bowl to the outside edge between the bowl and cap.

Likewise, in the interest of maintaining a silencer or separator that can be handled, removed, cleaned, and the like, it is key to limit any excess amount of oil or other previously atomized liquid clinging to various surfaces. The drain may be provided with a surface tension breaker. Typically, the greatest surface tension is between the liquid and itself. However, surface tension also exists between the material of the silencer-separator and the oil. Accordingly, the drain hole or drain port in the separator plate may be provided with a surface tension breaker positioned therebelow. The surface tension breaker may simply be a sharp-cornered projection extending out from the wall or inside surface of the neck to encourage any droplets forming in or around the drain port to adhere thereto and drip away. By making comparatively sharp corners having a small or no chamfer for a corner break, surface tension tends to draw liquids immediately toward the wall and away from the drain.

In one embodiment of a method of atomizing liquids in a flow of air, one may provide a source of air and a source of liquid, thereafter atomizing a portion of the liquid into droplets by the flow of air. Providing a first drift chamber requiring at least one change of direction prior to exiting the first drift chamber begins separation of droplets by size.

Then, providing a channel having a large aspect ratio of length of travel compared to thickness of the flow, and a large aspect ratio of width of the flow to the thickness of the flow provides centripetal separation therein, another separation step. Providing a second drift chamber requiring at least one change of direction of the airflow prior to exit therefrom may include various mechanisms such as a change of direction, or several, as well as changes in cross sectional area for the flow, thus speeding and slowing (or vice versa) the flow one or more times.

Each drift chamber may require one or more changes of direction, three changes of direction of the flow being typical. An air blade wall enclosing the entire flow of air and droplets contained therewithin may pass between the first drift chamber and the second drift chamber. An outlet port from the second drift chamber is typically offset to cause the flow to change direction at least three times in order to pass from the air blade through the exit or outlet port.

An eductor may b provided to serve as an initial atomization device forming droplets of the liquid in the airflow. Integrating the second drift chamber with a suitable type of separator plate divides the first drift chamber from the second drift chamber. That separator plate may include or have secured thereto a channel formed to extend between the chambers (separation chambers, drift chambers) on either extreme (typically top and bottom) of the separator plate. That channel may be characterized by a length and minimum characteristic thickness. The thickness serves best if substantially less than the length, and calculated to establish a laminar flow profile (see any text on fluid mechanics, Reynolds number below 2100). Laminar or turbulent, it is still effective to separate out comparatively larger droplets against the walls of the channel, while leaving entrained in the airflow comparatively smaller droplets sufficiently small such that aerodynamic drag of the air thereagainst is sufficient to overcome settling down by gravity or impingement against solid surfaces.

Certain methods of separating out comparatively larger liquid droplets from comparatively smaller liquid droplets in a flow of air may include providing an atomizer atomizing a liquid in a flow of air, passing the flow of air into a first drift chamber requiring at least one change of direction between the atomization and exit therefrom, passing the airflow through a channel having an aspect ratio of a minimum width to a length of travel of from about one third to about one twentieth, and passing the airflow through a second drift chamber requiring at least one change of direction between introduction into the second drift chamber, and exit from the second drift chamber. The method or process may continue by discharging the airflow containing only the non-separated, comparatively smaller droplets of liquid entrained therein into the atmosphere surrounding the second drift chamber.

An apparatus may include a bowl, a neck connecting the bowl to a flow of air an air blade constituting a channel having an aspect ratio of minimum thickness to length of travel ranging from about 0.3 to about 0.05 passing the airflow following atomization through the channel into a drift chamber requiring at least one change of direction prior to exit therefrom. Then, an exit port offset away from the air blade discharges the flow, after requiring at least one change of direction therebetween.

A cap, separable from the bowl, such that the cap and bowl together form the second drift chamber. The cap sits opposite (typically above) a floor operating as a separator plate. Together, the cap and separator plate bound from above and below an interior volume of the second drift chamber conducting from its atomizer (source) the flow of air. The air blade channel may be constructed to be curvilinear. This provides more available width (horizontally) perpendicular to the thickness (also measured horizontally). Thus, when the channel is curved in a circumferential direction, the airflow is axial (vertical) through the channel.

The second drift chamber is configured to have an exit port discharging the airflow in an axial direction substantially parallel to the flow in the channel. The exit port is best offset from the channel to require at least two changes (typically three or more) of direction of the airflow to pass from the channel of the exit port. Also, the flow must accelerate and decelerate, sometimes more than once each. One may consider the floor of the bowl, through which the air blade channel passes to be a separator plate separating the atomizer from the second drift chamber. However, it is also proper to speak of everything between the first and second drift chambers to be a "separator plate." A separator plate is not simply a plate, or need not be. It may have various apertures, channels, and walls to effect a "separation" process in addition to the separation processes conducted in each drift chamber. It is simply more compact, and may rely on various processes of acceleration, flow profiles, and the like to encourage separation of larger droplets out of the flow. Larger droplets are those that tend to drift out of the air after discharge, and therefore need to be separated out and returned to the reservoir of liquid to be atomized again.

A drift chamber formed in the atomizer will typically receive atomized liquid in the airflow and collect a portion of the atomized liquid by impact against a wall, from whence returning the collected atomized liquid to a reservoir. Sufficiently small and dynamic atomized droplets of liquids (still suspended in the airflow) pass through the separator plate to the second drift chamber. Some pass all the way through to the exit, the objective being to pass only those that will remain suspended in the room air, not allowing spitting or settling of the liquid droplets on furniture and other surroundings.

Silencing and separation processes in a cold-air, essential-oil, diffuser apparatus and method pass flow through a channel having comparatively high aspect ratios of length to thickness and width to thickness. Curved, tapered, non-parallel, and quasi random surfaces reduce probability and power of resonant frequencies. Offsetting flow through a channel is followed by impingement against an obstructing surface, redirection elsewhere within a drift (separation) chamber, and exiting through a smaller, and differently oriented exit port. Silencing is improved by changes of cross-sectional area creating high-pass and low pass acoustic filters, changes of direction, and absorption of acoustic energy in fluid-droplet-laden air.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 1:
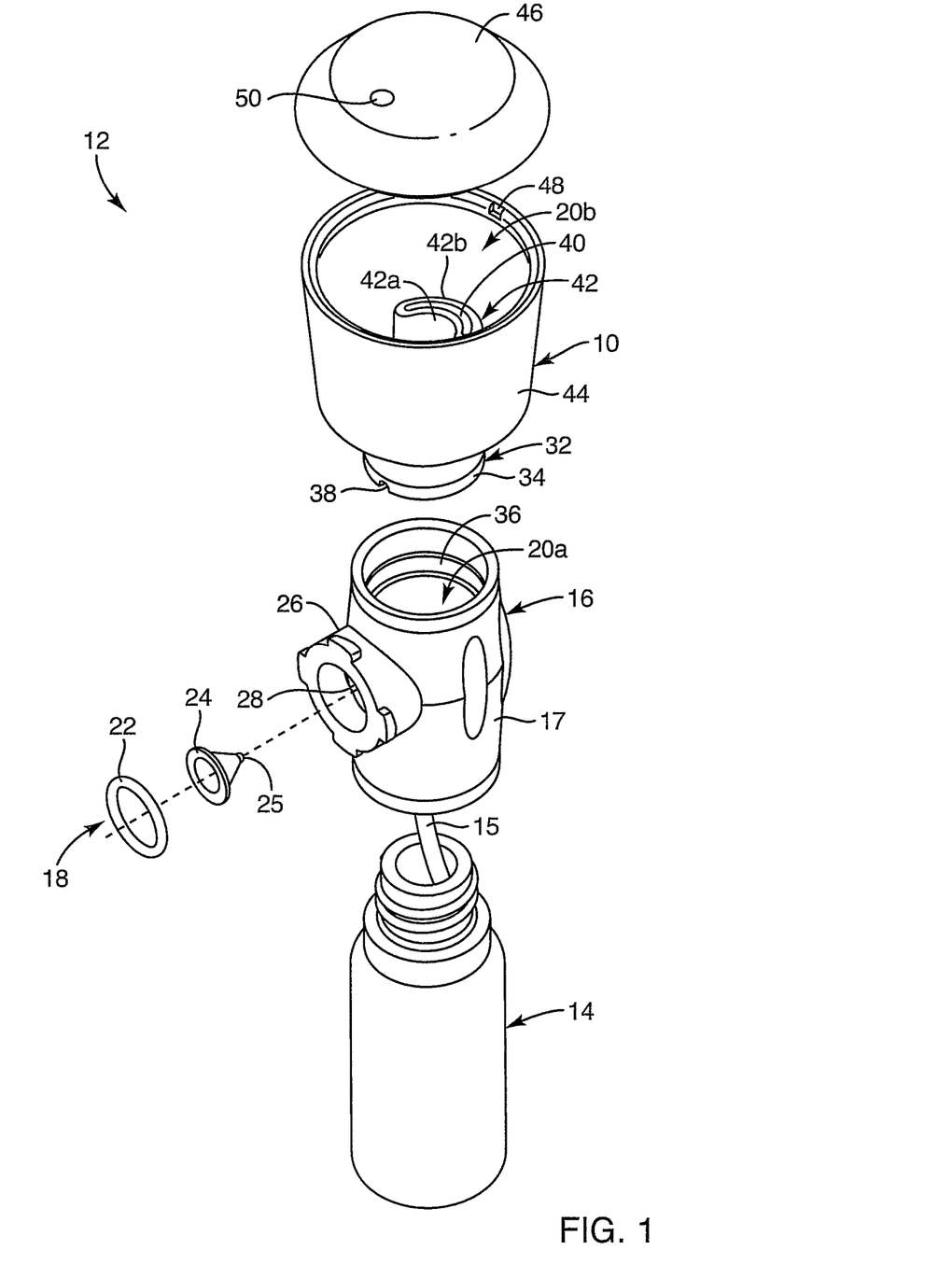
FIG. 1 is an upper perspective, exploded view of one embodiment of a complete diffuser system fitted with a silencer-separator in accordance with the instant invention.
Figure 2:
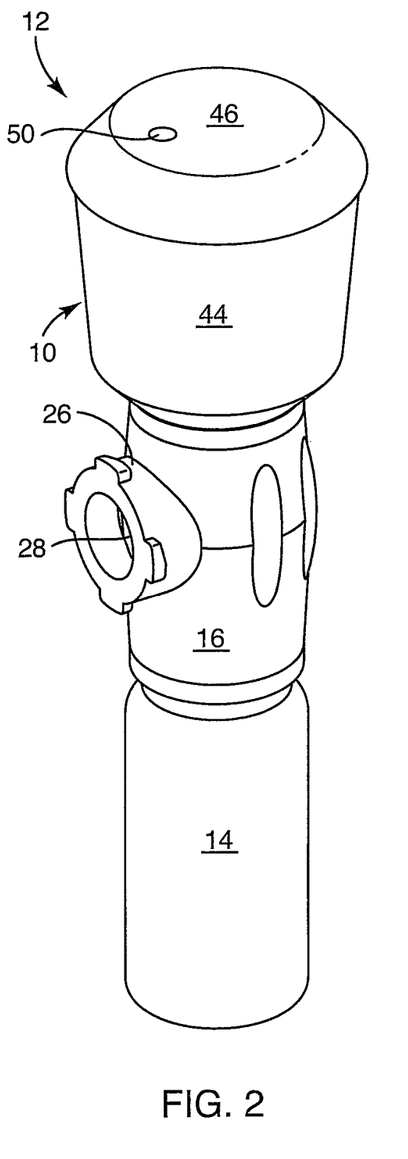
FIG. 2 is an upper, perspective, assembled view thereof.
Figure 3:
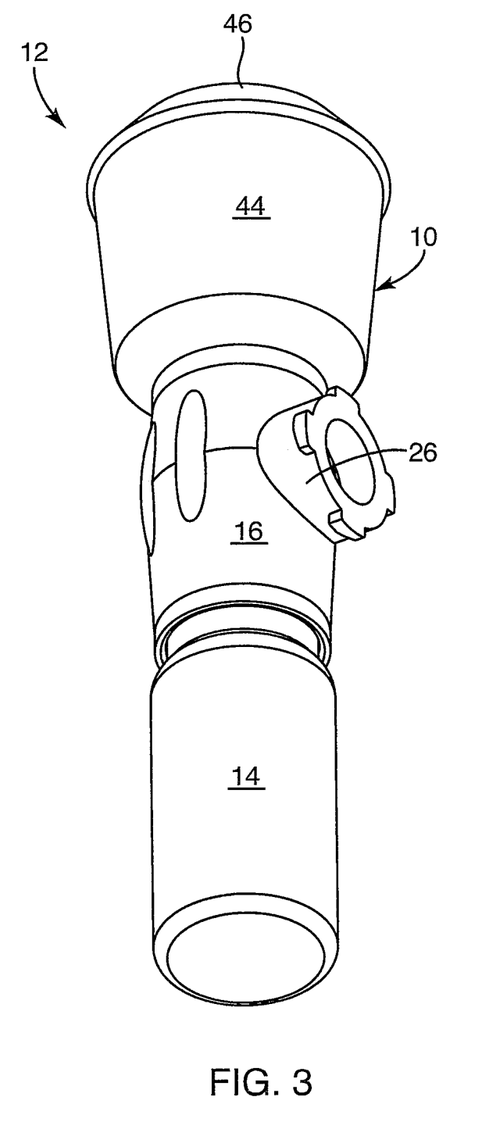
FIG. 3 is a lower, perspective, assembled view thereof.
Figure 4:
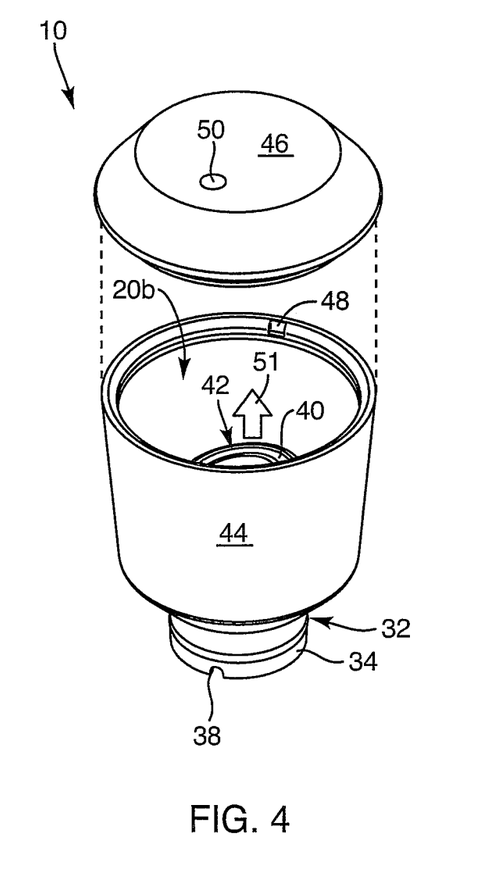
FIG. 4 is an upper, perspective, exploded view of the silencer-separator.
Figure 5:
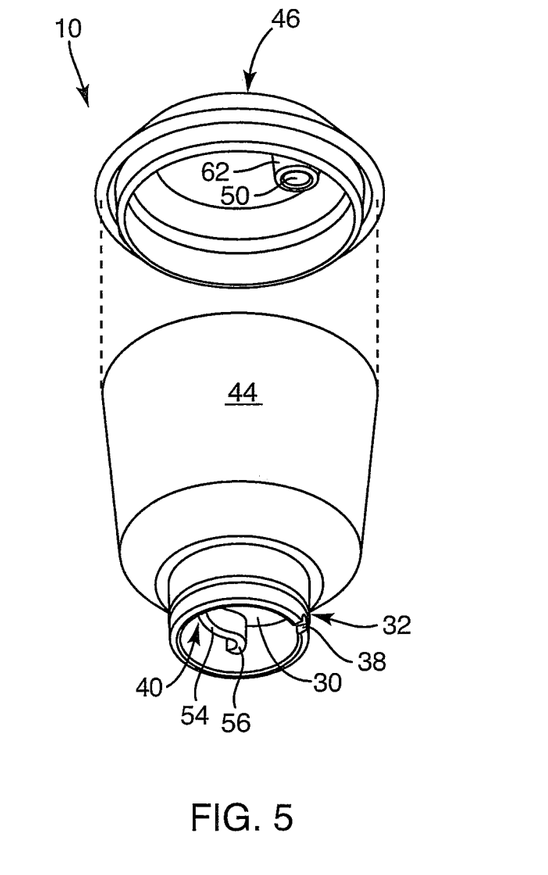
FIG. 5 is a lower, perspective, exploded view thereof.
Figure 6:
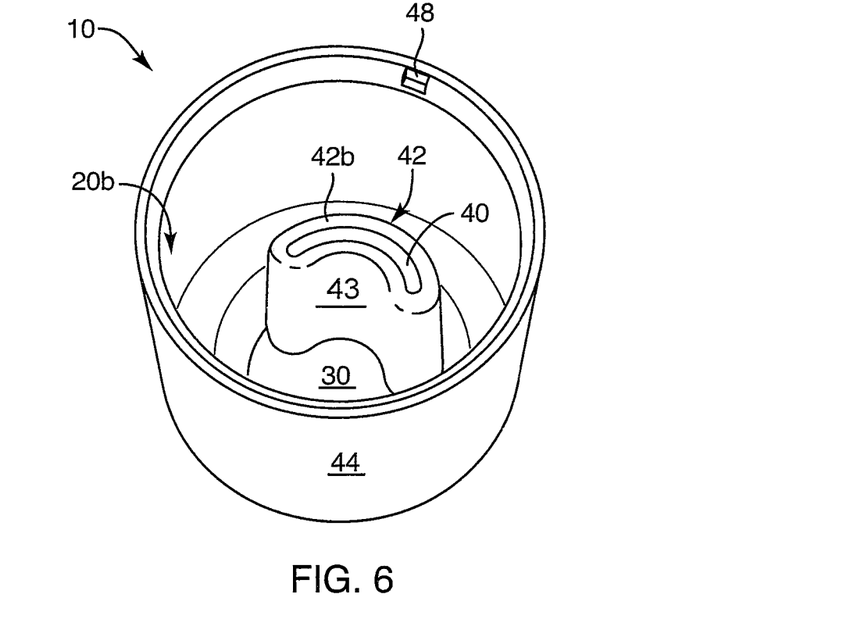
FIG. 6 is an upper, more steeply angled, perspective view of the lower or bowl portion thereof.
Figure 7:
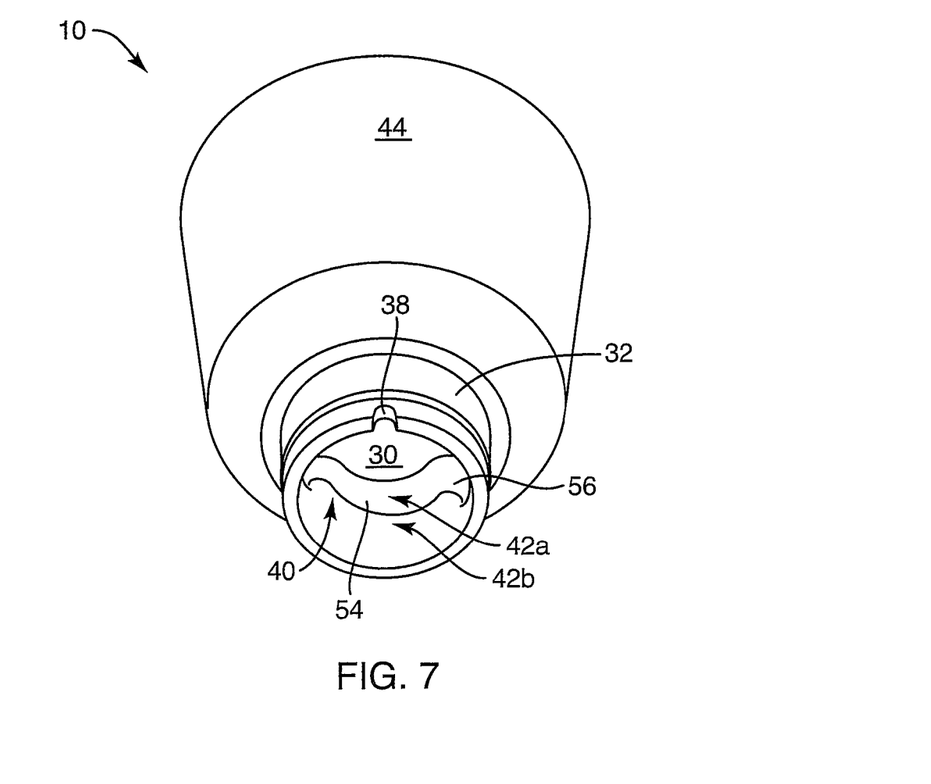
FIG. 7 is a lower, perspective view of the bowl of FIG. 6.
Figure 8:
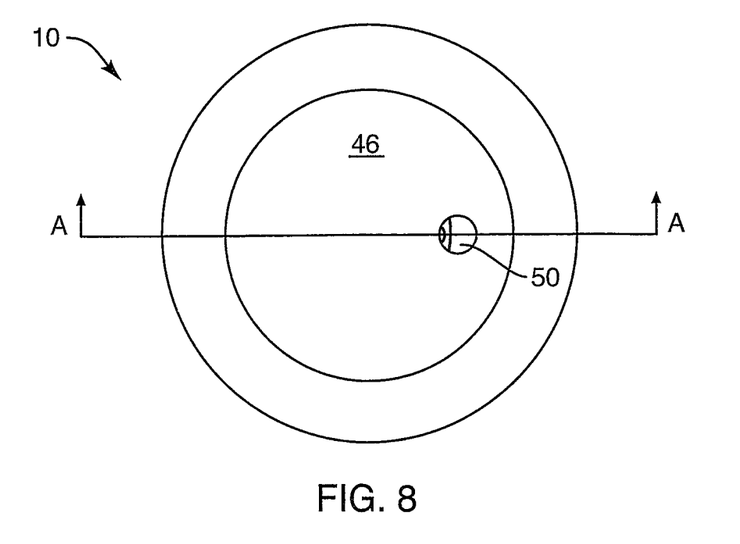
FIG. 8 is a top plan view of the cap, and therefore the silencer-separator in accordance with the invention.

Referring to FIG. 1, while continuing to refer to FIGS. 1 through 14 generally, a silencer 10 or separator 10 may be configured as an air-blade, silencing, separator apparatus and method. Accordingly, it will be appropriate to speak of the subsystem 10 as a silencer, a separator, an air-blade, or the like. The subsystem 10 may also be referred to as a silencer-separator, since it functions as both, and was designed, experimented, evaluated, operated, redesigned, modified, dozens upon dozens of times in order to obtain its combination of silencing and separating effects.

By silencing is meant the reduction in sound propagated outside a diffuser 12 or system 12 in operation. By separating is meant the separation from a flow of air, certain, entrained droplets in the flow of air. Typically, as used herein, the expression separator or separating refers to removing "comparatively larger" droplets. Comparatively 
larger droplets refer to those droplets that are sufficiently large that their mass, and therefore their weight under the influence of gravity, are sufficiently large compared to their aerodynamic drag in a flow of modest to velocity, typically the circulation of room air, that such droplets will fall out of the flow of air within the room, typically 15 to 20 feet.

However, comparatively smaller droplets remain in the airflow constitute the objective. Thus, comparatively smaller droplets are those that are sufficiently small that they will drift in a flow of air at modest velocities, typically associated with ventilation motion of the air in a ventilated room, indefinitely. Indefinitely means at least an hour or more, and will typically be several hours, or until the room air has been effectively exchanged.

In a system 12 equipped with a silencer-separator 10, the system 12 is effectively constituted as a cold-air, diffusion apparatus 12, also referred to simply as a diffuser 12. A diffuser 12 may draw from a reservoir 14 containing a suitable liquid. Liquids typically may include essential oils, mixtures of solvents with the essential oils, emulsions of water, other liquids, or the like. Typically, the content or liquid in a reservoir 14 is drawn through a tube 15 or line 15 penetrating to a location near the bottom of the reservoir 14. An atomizer 16 draws liquid content from the reservoir 14 through the line 15 to be atomized. By atomization is meant the breaking up of a liquid, flow of liquid, or the like into a random distribution, which will typically be a Gaussian distribution, also known as a normal distribution.

Atomization may be done by a venturi or an eductor. A venturi is a conduit narrowing to a throat through which a flow of fluid passes, the conduit progressing from a comparatively larger diameter to a smaller diameter and ultimately to a narrowest diameter, followed by an increase in diameter. By the word diameter is meant hydraulic diameter. A hydraulic diameter is four times the area divided by the wetted perimeter. In a circular cross-sectional area, hydraulic diameter equals circular diameter. In a square cross section, hydraulic diameter equals the length of one side.

In any other shape of a cross section, the hydraulic diameter provides a value that may be used for effective diameter in hydrodynamic or aerodynamic equations of flow. Hydraulic diameter relates the cross-sectional area to the shape of the perimeter or circumference of or about a flow. Thus, in speaking of diameter, the expression means effective diameter or hydraulic diameter. That is, any time the word diameter is used, what is meant is the effective diameter.

A venturi relies upon dynamic pressure head. Typically, in a flow through a venturi, dynamic pressure head is substantially constant. There is some amount of drag, but it is substantially negligible in many instances. Thus, assuming a constant, dynamic pressure head means that the static pressure contribution and the velocity contribution to dynamic pressure head add to the same constant value throughout. Thus, whenever the cross-sectional area narrows, the velocity must increase. Thus, the velocity head component must increase, causing a reduction in the static pressure head contribution.

The result of the reduction in static pressure head at the narrowest portion or the throat of a venturi results in a low pressure region that tends to draw against the walls. Thus, a penetration, tube, pipe, or a port in a wall, or the presence of a tube, inlet, or other access by a second fluid at the exact throat (narrowest portion) of a venturi will result in drawing that fluid into the flow.

An eductor is an entirely different mechanism. An eductor is a device found in virtually all gas stoves, gas furnaces (e.g., propane, natural gas, butane, etc.) and has been for decades, in fact, over a century. Likewise, eductors are used in various pumping systems, particularly for pumping fluids that will damage pumps. Sewage is one example.

For example, pumping a flow of sewage sludge is not appropriate for a mechanical pump. Damage by wear and corrosion would be swift and certain. Instead, a cleaner fluid may be injected as a high speed jet relative to a comparatively low speed flow of sludge. The high speed jet imparts momentum from itself (e.g., small mass, high velocity) to the flow of sludge (e.g., large mass, comparatively low velocity).

An eductor thus relies on direct momentum transfer between a first flow at a comparatively higher velocity into a second flow at a comparatively lower velocity. Momentum transferred from the higher speed jet into the lower speed surrounding fluid results in motion of the comparatively slower mass of fluid, resulting in drawing in more of that surrounding fluid into the jet as it progresses forward.

Eductors 18 have been described in considerable detail, along with their operation, in the references incorporated hereinabove by reference. Typically, an eductor 18 may be made up of a variety of components, resulting in a flow of air therethrough shattering or comminuting liquid, received through the tube 15, in an eductor jet 28, not shown in entire detail here, but included in great detail in the references incorporated herein by reference.

The atomizer 16 may include a housing 17, as a part of which the eductor 18 may fit its own seals 22 air jet nozzles 24 including a jet aperture 25 all fitted into a housing 26 for containment. The eductor nozzle 28 receives air from the jet opening 25 through the eductor nozzle 28, thus drawing with it liquid captured therebetween, that is, between the air nozzle 24 and the eductor nozzle 28. Thus, out of an opening in the eductor nozzle 28 sprays an airflow containing a distribution of droplets of the liquid content drawn from the reservoir 14.

The droplets from the eductor 18 enter a separation chamber **20*a* or drift chamber 20*a*. The drift chamber 20*a* may also be referred to as a separator 20*a*. A separator 20, generally, operates by several mechanisms. First of all, the specific separation chamber 20*a* as constituted by the housing 17**, presents a wall against which the flow will impinge. Comparatively larger droplets will tend to strike the wall. Comparatively smaller droplets will tend to remain in the flow of air.

That is, comparatively larger droplets having more mass, and therefore more weight, associated with greater momentum within themselves, are sufficiently heavy that they cannot change direction due to the insufficient aerodynamic drag of air flowing thereby. Accordingly, comparatively larger droplets strike a wall, coalesce there or shatter. To the extent that the droplets coalesce, they will drift downward toward the reservoir 14. To the extent that the droplets shatter, comparatively larger portions may again be subjected to coalescing against the wall. Sufficiently small droplets will be entrained (carried by aerodynamic drag) within the airflow, eventually finding their way out of an exit from the drift chamber **20*a*. A separator plate 30 may divide the separator chamber 20*a* of the atomizer 16 from a second separation chamber 20*b* or drift chamber 20*b* of the silencer-separator 10**. Trailing letters or reference numerals indicate a specific instance of the item type identified by the numeral.

The silencer-separator 10 may begin at its lower extremity with a neck 32. The neck 32 may include a collar portion 34 or collar 34 that has a smaller or larger diameter than does the neck 32. In the illustrated embodiment, the collar 34 has a smaller diameter, in order to fit into the housing 17 of the atomizer 16. In other embodiments, the collar 34 may have a larger diameter than the neck 32, thus forming a detent 34 to constrain the neck 32 within the housing 17 of the atomizer 16. In other embodiments, threads may substitute for any other retainers.

However, in the illustrated embodiment, one purpose for the collar 34 is to provide a close fit against the surface 36 in the housing 17. Likewise, a registration 38 or notch 38 in the neck 32 fits against a matching or mating protrusion on the surface 36. Thus, by not being threaded, the neck 32 may slide into the housing 17, with the collar 34 snuggly fitting against the surface 36, and being rotatable for registering the registration 38 or notch 38 therein.

Registration 38 assures that the channel 40 or air blade 40 itself is opposite the eductor nozzle 28 of the atomizer 16. This, as it turns out, is important for reducing sound. Sound waves propagate up through the channel 40 or air blade 40. The channel (cavity) 40 may be called an air blade 40 and creates a blade of air or an air blade, because it has a comparatively narrow thickness relative to both its overall width, and its overall length in the direction of flow (e.g., vertically).

The air blade 40 or channel 40, by being positioned obliquely, in fact a right angle, in the illustrated embodiment, with respect to the flow of the eduction spray, provides much damping, and uncoupling of the soundwaves by virtue of the difference in characteristic lengths between it and the surrounding drift chamber 20b. Various characteristic lengths (e.g., diameter, varied diameter along its height, depth, varied depth in view of the capered bottom surface, and so forth) exist throughout.

Referring to FIG. 1, while continuing to refer generally to FIGS. 1 through 14, a silencer-separator 10 may include a channel 40 or air blade 40 defined by a wall 42 around a tower 43. The wall 42 may include an inner portion 42a and an outer portion 42b. Typically, the outer portion 42b will extend down and through the separator plate 30. Accordingly, the actual outer wall 42b may eventually be coincident or share an inner surface with the neck 32 at the bottom of the silencer-separator 10.

Referring to FIGS. 2 and 3, and FIGS. 1 through 14 generally, one will see that assembled, the system 12 may include a reservoir 14, threaded onto an atomizer 16, with a silencer-separator 10 fitted into the upper opening of the atomizer 16. Effectively, the bowl 44 or bowl portion 44 of the silencer-separator 10 defines the wall surrounding the second drift chamber 20b. By drift chamber 20 is meant that an airflow containing droplets flows through the drift chamber 20, permitting comparatively larger (higher momentum, lower drag) droplets to drift out of the flow of air to impinge against solid surfaces, there coalescing to become a film, rivulets, and drops that eventually drip downward to return to the reservoir 14. The bowl 44 is closed on top by a cap 46. The cap 46 is comparatively snuggly fitted in order to not pass any significant amount of fluids through the seal or fit therebetween.

Referring to FIGS. 4 through 10, while continuing to refer generally to FIGS. 1 through 14, the bowl 44 and cap 46 may be provided with a registration 48 or notch 48 adapted to receive a protrusion in the cap 46, fitted thereto. One will note that the registration 48 is illustrated as a notch, but could be a protrusion, a spline, a key, or the like. Typically, a collar on the cap 46 may slide with a friction fit into the bowl 44.

One benefit of a sliding fit, snap fit, or the like is that the registration 48 may be matched with a corresponding registration 49 on the cap 46. Thus, the bowl 44 and cap 46 may be visibly rotated with respect with one another in order to match up the registration 48 at the appropriate location. The effect of the registration 48 is to establish the position of the air blade 40 with respect to the outlet 50. Typically, the registration 48 and its matching pin 49 may be reversed or may be changed in any suitable manner, so long as registration therebetween is promoted.

Effectively, the outlet 50 serves best if offset by at least 90 degrees from the plane or center plane that would effectively form a reflectively symmetric surface passing vertically through the tower 43, air blade 40, and its walls 42. As a practical matter, it is proper to speak of the air blade 40 as the channel 40, or as the flow of air 51 therethrough. Thus, the flow 51 through the channel 40 represents an air blade 40, 51. Similarly, one may speak of the air blade as the structure 42 or walls 42 that form the channel 40 that passes the flow 51. Thus, herein, the term air blade 10, 40, 43, 51 should be clear from its context.

It has been found that the outlet 50 serves best if offset by 180 degrees from the channel 40, or the center line or center plane through the channel 40. One may think of a center plane through the channel 40 as a vertical plane extending upward and horizontally bisecting both the inner wall 42a and outer wall 42b around the channel 40. The separator plane or dividing plane would thus form a vertical plane of symmetry for the air blade 40, the flow 51, the walls 42, the bowl 44, the cap 46, and so forth.

Referring to FIGS. 5 through 10, while continuing to refer generally to FIGS. 1 through 14, the silencer-separator 10 is not entirely symmetrical or axially symmetrical. For example, the cap 46 and bowl 44 are largely point symmetrical or axially symmetrical. Nevertheless, the walls 42 are clearly not line or point symmetrical, being offset from the center, and curved along a circumferential direction to be uniformly spaced away from the bowl 44 itself.

The bowl 44 and cap 46 may be fitted together with a notch registration 38 and a corresponding pin 49 or peg 49. Meanwhile, proceeding circumferentially around virtually the entire circumference of the cap 46 may be a capillary break 52. A capillary break 52 constitutes a gap 52 sufficiently large that capillary action of the contained fluid droplets coming from the eductor and coalescing in the bowl 44 will not cross. Accordingly, oil will not collect or seep out of the gap or the sealing surfaces between the bowl 44 and the cap 46.

For example, the vertical surface 53 may be comparatively tight, and therefore may attract, due to surface tension, collection of a certain quantity of oil or other contents being coalesced from droplets. However, the capillary break 52 interferes with transport to anywhere outside the bowl 44.

Figure 9:
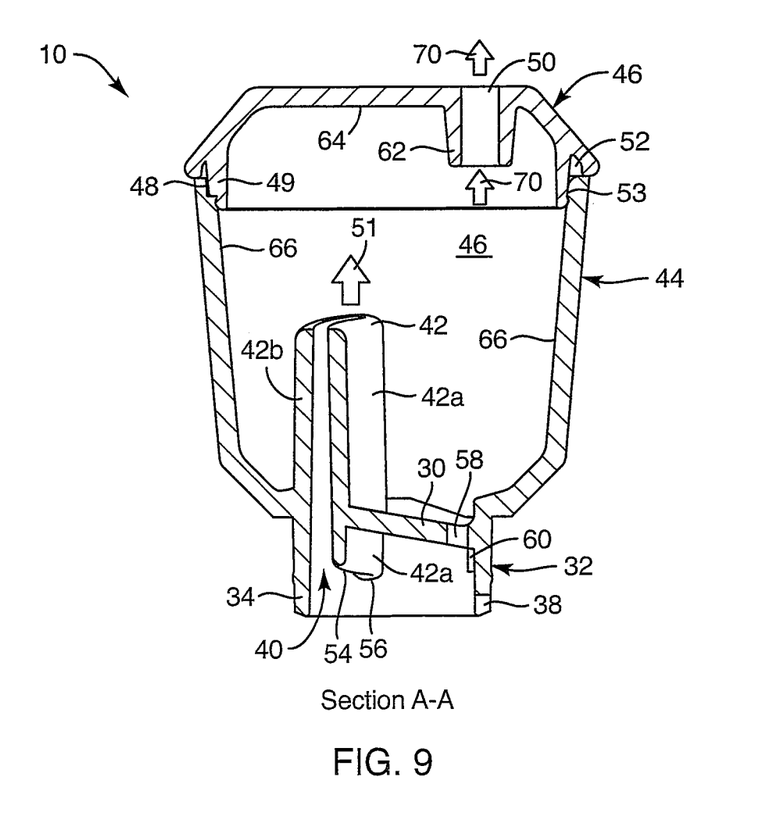
FIG. 9 is a side, elevation, cross-sectional view of a silencer-separator in accordance with the invention.
Figure 10A:
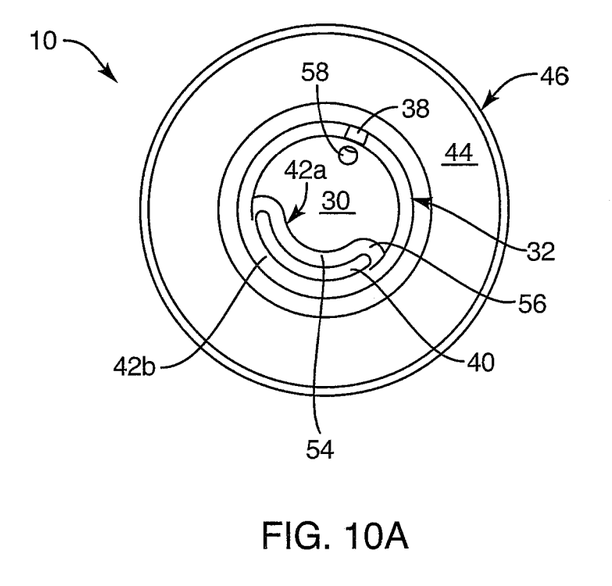
FIG. 10A is a bottom plan view of a silencer-separator in accordance with the invention.
Figure 10B:
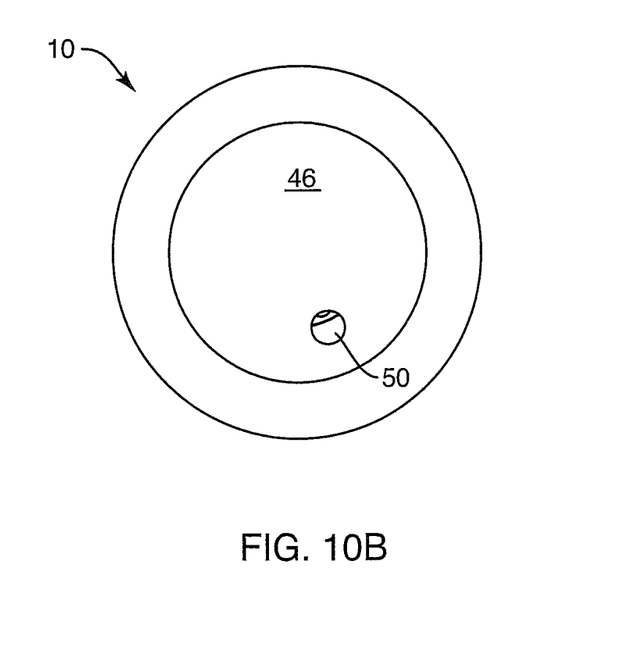
FIG. 10B is a top plan view thereof.
Figure 11:
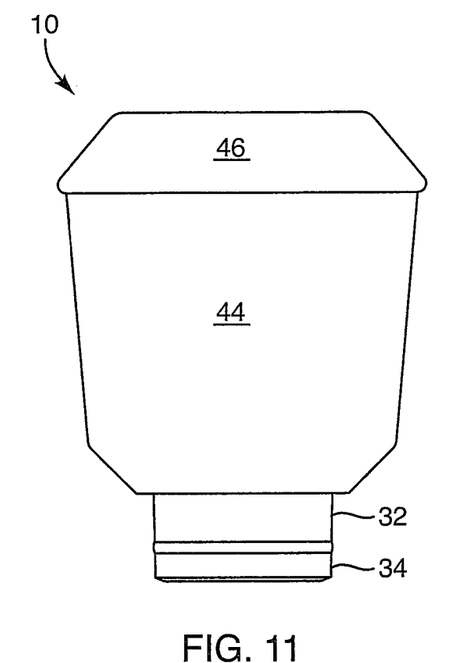
FIG. 11 is a front elevation view thereof.
Figure 12:
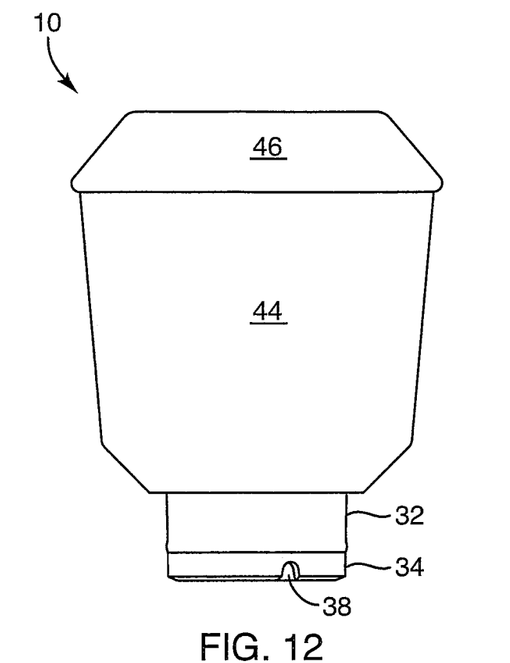
FIG. 12 is a rear elevation view thereof.
Figure 13:
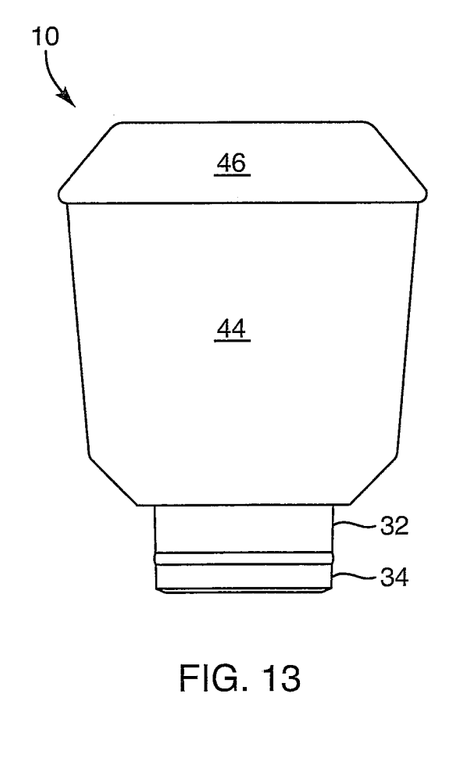
FIG. 13 is a right side elevation view thereof.
Figure 14:
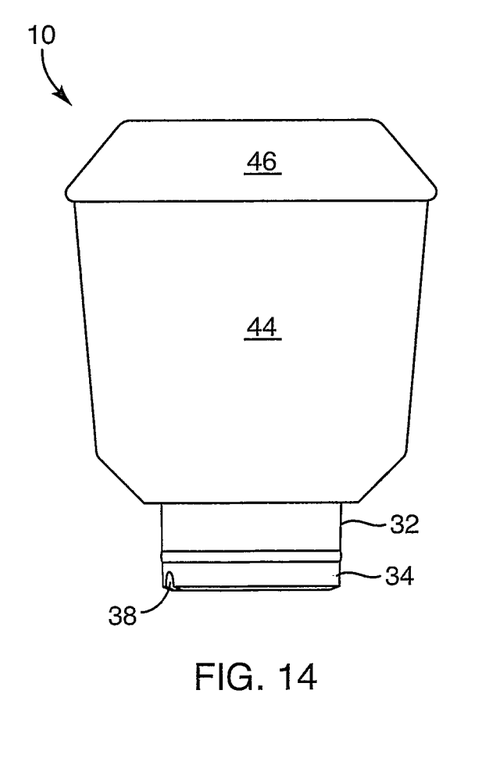
FIG. 14 is a left side elevation view thereof.

Regarding asymmetric features of the silencer-separator 10, one will immediately note that in FIG. 9 the inner wall 42a angles downward. The lower edge 54 acts as a drip edge 54. For example, the channel 40 between the inner wall 42a and outer wall 42b constituting the walls 42 or wall region 42 develops a slot flow profile as well understood in engineering.

Any basic, engineering, fluid-mechanics book will describe conditions and show the flow profile for a laminar flow and for a turbulent flow in a narrow passage. In either event, a boundary layer near the surfaces of the walls 42a, 42b will form, moving very slowly and collecting liquid droplets that touch the walls 42a, 42b.

Droplets thereby adhere to the walls 42 and other liquids coalesce thereagainst. A direct result is a flow down the inside surfaces of the channel 40. That flow along the outer wall 42b will eventually find its way down into the housing 17 and neck 32 of the atomizer 16, and thereby to the reservoir 14. Meanwhile, any coalesced droplets that impinge against the inner surface of the bowl 44 will drain downward toward the drain 58.

One will note that the drip edge 44, by being angled downward from one extreme to the other, creates a drip point 56 at the lowest location 56 of the drip edge 54. Droplets coalescing against the inner wall 42a, within the channel 40 will flow down to the drip edge 54, and thence to the drip point 56, where they will form droplets that will readily drop back into the housing 17 from the neck 32. Droplets tend not to stop along the drip edge 54, but collect and move downward toward the drip point 56. Thus, droplets collected from the channel 40 will typically adhere to the wall 42, move toward the outer wall 42b, and thereby drip back through the neck 32 and into the housing 17 and reservoir 14.

The drain 58 may be provided with a breaker 60 or surface tension breaker 60 constituted by a sharp edge or multiple sharp edges on a protrusion 60 away from the neck 32. This protrusion 60 may have sharp edges in order to promote the formation of droplets therearound, stripping them from the drain 58, so they do not collect, become blocked, or otherwise form larger droplets suspending from the drain 58. The breaker 60 operates as a surface tension breaker 60 providing a solid surface promoting flow away from the drain 58.

In general, the capillary break 52, the surface tension breaker 60, the drip edge 54 and drip point 56, and so forth are innovations deemed appropriate in order to encourage complete draining of liquids from the silencer-separator 10. Typically, the system 12 may be taken apart, the reservoirs 14 may be changed out with different contents, and so forth. By encouraging prompt and complete draining of all liquids back to the reservoir 14, the silencer-separator 10 is maintained cleaner, will be less likely to drip or otherwise transfer oily contents to the hands or clothing of a user, or to a surface on which any component may be temporarily set when dismantled.

Referring to FIG. 9, while continuing to refer generally to FIGS. 1 through 14, one will note that the port 50 or outlet 50 also includes a wall 62 protruding into the drift chamber 20b formed by the bowl 44 and cap 46. This provides several benefits. First, the wall 62 provides a requirement for a change of direction, and multiple changes of direction of airflows. For example, an airflow 51 exits substantially vertically. Thence, the flow 51 will impinge against the cap 46, particularly, an inner, horizontal surface 64 thereof.

Thereafter, the flow 51 will be diverted to flow in other directions throughout the drift chamber 20b. To the extent that airflow progresses radially, it may impinge against the inner surface 66 of the bowl 44. Ultimately, a flow 70 may exit the outlet 50. However, at least three changes of direction must occur in most of the flow 51 in order for the flow 51 or droplets and air within the flow 51 to exit the channel 50, since the air blade 51 comes to a halt due to striking the inside surface 64 of the cap 46, progress horizontally, radially, and the like in order to reach the outlet 50. The flow must then turn to progress vertically out through the port 50.

Moreover, the change of shape between the comparatively thin but wide air blade 51 from the channel 40 and the comparatively narrow, typically circular or otherwise cylindrical shape of the outlet 50, requires expansion of the flow into a larger area, out of a comparatively smaller cross-sectional area. It then reduces from that comparatively larger cross-sectional area back into an even smaller cross-sectional area of the exit 50.

This repeated change of cross-sectional area available to accommodate the flow also results in drifting, slowing, and jinking (zig-zagging, sharp turns back and forth, darting), which action therefore provide more dwell time, repeated acceleration and deceleration of flow, and so forth to promote more drifting and smashing by comparatively larger droplets against solid surfaces.

Only droplets small enough that their mass, momentum, and fluid dynamic drag permit them to remain with the air flow through all its twists, turns, stops, starts, accelerations, and decelerations will remain in that flow when it exits the systems 10, 12.

This is the ultimate definition of "small" droplets, those that exit the separator 12 with the air flow. At any space, conduit, path, location, or the like, the "comparatively larger droplets" are those that strike a solid surface and coalesce. "Comparatively smaller droplets" remain entrained in, and exit that space with, the flow of air therethrough.

The silencer-separator 10 illustrated has proven highly effective in eliminating the sound of hissing generated by an atomizer 16, and particularly the eductor 18. It is also very effective at eliminating comparatively larger droplets in the airflow 70 proceeding from the outlet 50. Those comparatively larger droplets are those that would otherwise drift downward at an unacceptable rate to land on furniture, counters, and flooring. The objective is for all droplets released to evaporate or drift with room air indefinitely or sweep out with ventilation air exiting the treated space.

The sound is minimized, typically reduced by from about six to about ten decibels in volume (intensity, amplitude), and typically provides on the order of about eight decibels of reduction of sound when the outlet 50 is 180 degrees out of phase with respect to the tower 43 of the air blade 51. Meanwhile, the elimination of comparatively larger droplets or "spitting" droplets that are sufficiently large to settle out on furniture or other surfaces nearby is eliminated so long as the cap 46 has been rotated to place the outlet 50 at about 90 degrees or greater out of phase with the center plane of the air blade 40.

Other features of a silencer-separator 10 in accordance with the invention are the various changes in cross-sectional area, shape, and so forth. By providing suitable taper to the shape of the bowl 44, the variation in diameter tends to avoid establishing a single resonant length that may promote resonant frequencies of audible sound waves during operation of the system 12. Likewise, by canting or tilting the separator plate 30 that operates as a floor 30 of the bowl 44, a single resonant length or height is less likely. Similarly, below the floor 30 (i.e., separator plate 30), vertical height is affected by the angled separator plate 30.

The shape of the tower 43 and air blade 51 is capable of accomplishing several functions. First, maintaining a distance from the exit 50 or outlet port 50 is accommodated by wrapping the walls 42 along the path substantially parallel to the surface 66 inside the bowl 44. Also, this provides for maintaining distance away from the outlet 50. Although a straight (non curved) channel 40 may operate to provide the separation function of the channel 40, coalescing droplets along the walls 42a, 42b, the sound is prevented from obtaining consistent characteristic lengths by the curvature, and its resulting distribution of the flow 51 throughout the drift chamber 20b. In other words, care has been taken to reduce the incidence of single, characteristic lengths that might promote or support resonant frequencies that may increase propagation of sounds.

Referring to FIGS. 8 through 14, the various views of the silencer-separator 10 illustrate the relative dimensions and shapes involved. For example, the neck 32 is comparatively smaller, and capable of fitting within a housing 17 of an atomizer 16 available. Meanwhile, the comparatively larger diameter of the bowl 44 provides substantial drift space, substantial increase in cross-sectional area of the flow, multidirectional dispersion of the flow 51, and so forth. Meanwhile, the rear elevation, front elevation, right side elevation, and left side elevation views show substantial symmetry, with only small variations. Nevertheless, internally, the pleasing symmetry of the exterior is absent and does not limit the ability to form non-symmetric shapes, flow areas, transitions, changes of direction, and the like therewithin.

One will also note the manufacturing elegance of the outer wall 42b being essentially coincident with the neck 32 generally. Meanwhile, the formation of the channel 40 by the inner wall 42a, may be molded from the two sides or surfaces of the separator plate 30 that forms the floor 30 of the bowl 44, and the sealing of the first drift chamber 28 in the housing 17. An additional separator plate, or even a micro-cyclone may still be placed below the system 12.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of atomizing liquid in a flow of air, the method comprising:
    providing a source of the liquid and a source of the air, the air pressurized to urge a flow characterized by thickness, width, and length, generally mutually orthogonal at any point in the flow, wherein a cross-sectional area is characterized by the width and length, and a distance traveled is characterized by the length;
    providing an atomizer dispersing into the flow a portion of the liquid as droplets entrained therein;
    providing a first drift chamber segregating the droplets by receiving the flow and changing a direction thereof prior to the flow exiting therefrom;
    providing a tower, having an inlet formed by a curved drip edge, and a tower wall, defining thereinside a channel protruding upward from the first drift chamber into a second drift chamber, formed as a bowl having a bowl wall surrounding and spaced from the tower, to receive and contain the flow, the channel having first and second ends defining a first aspect ratio of length to thickness thereof greater than one, and a second aspect ratio of length t o width thereof, at least one of the first and second aspect ratios selected to form a boundary layer in the channel segregating the droplets; and
    providing the second drift chamber connected to receive the flow from the second end, opposite the first drift chamber at the first end, imposing at least two changes of direction of the flow prior to exit therefrom
    wherein the tower is shaped to protrude straight along the length of the flow therethrough and is curved along the width, thereby forming the flow into an air blade, within the wall enclosing the entire flow of air, the droplets contained therewithin, passing as a blade of air, having a thickness less than a width thereof and less than a length of the flow therethrough, to maintain the boundary layer of the blade removing comparatively larger droplets from comparatively smaller droplets between the first drift chamber and the second drift chamber.

2. The method of claim 1, wherein the first drift chamber is shaped to segregate the droplets by imposing more than one change of direction and more than one change of velocity of the flow.

3. The method of claim 2, wherein the second drift chamber is molded to render the bowl continuous with the tower, and further segregates the droplets by imposing two changes of velocity of the flow between exiting the channel and exiting the bowl.

4. The method of claim 3, wherein each of the first drift chamber and the second drift chamber imposes upon the flow at least three changes of direction, an acceleration, and a deceleration.

5. The method of claim 1, further comprising providing an outlet configured as an exit port from the second drift chamber, the outlet offset from the tower.

6. The method of claim 5, further comprising providing an eductor as the atomizer.

7. The method of claim 4, wherein the second drift chamber comprises a separator plate extending horizontally to divide the first drift chamber below from the second drift chamber directly thereabove, the channel passing vertically through the separator plate.

8. The method of claim 1, wherein the first drift chamber is separated from the second drift chamber by the tower extending therebetween and characterized by tower walls defining a channel length extending straight and channel thickness, less than said channel length and calculated to establish a laminar flow profile separating out comparatively larger droplets against the walls, while leaving entrained in the flow comparatively smaller droplets small that aerodynamic drag of air thereagainst is sufficient to overcome settling by gravity or impingement of the comparatively smaller droplets against solid surfaces.

9. A method of separating out comparativeiy larger liquid droplets from comparatively smaller liquid droplets in a flow of air, the method comprising:
    providing an atomizer atomizing a liquid in a flow of air;
    passing the flow of air into a first drift chamber, defining axial, radial, and circumferential directions and requiring at least one change of direction between the atomizing and exiting therefrom;
    passing the flow upward through a tower, formed as a circumferentially continuous tower wall defining a channel therein, and protruding vertically upward from the first drift chamber and protruding into a second drift chamber, the channel having an aspect ratio, constituted by at least one of a thickness to a width and the thickness to a length, respectively, segregating out comparatively larger droplets adhering against the wall from comparatively smaller droplets remaining in the flow in the channel;
    wherein the tower is shaped to protrude straight along the length of the flow therethrough and is curved along the width, and has an inlet formed by a curved drip edge
    passing the flow vertically into and subsequently through the second drift chamber, having a chamber waiI surrounding the tower and spaced radially therefrom, requiring at least one change of direction between 
introduction of the flow into the second drift chamber and exit thereof from the second drift chamber; and discharging, from the second drift chamber, vertically through an outlet offset radially away from, and smaller in cross section than, the channel, the flow containing only the comparatively smaller droplets of liquid entrained therein into an atmosphere surrounding the second drift chamber.

10. A method of separating out comparatively larger liquid droplets from comparatively smaller liquid droplets entrained in a flow of air, the method comprising:

selecting a device comprising, in vertically upward order, a neck, a bowl downstream from the neck, a channel defined by a tower comprising a tower wail protruding downstream from the neck into the bowl, and a cap forming a top on the bowl, wherein the neck is shaped and connected to receive and conduct a flow of air containing droplets of a liquid and pass the flow into the channel, the channel being characterized by a thickness, less than both a width and a length thereof, and capable of segregating the droplets by passing comparatively smaller droplets in the flow while adhering comparatively larger droplets to the tower wall along the length, the bowl being positioned to receive the flow from the channel, and the cap being positioned to redirect the flow exiting the channel;

wherein the tower is shaped to protrude straight along the length of the flow therethrough and is curved along the width, and has an inlet formed by a curved drip edge operably connecting the device to receive the flow and the liquid, as droplets entrained in the flow, through the neck into the channel;

separating out from the flow, by the tower, the comparatively larger droplets from the comparatively smaller droplets remaining in the flow by coalescing the comparatively larger droplets against the wall; and directing the flow from the channel toward an exit offset horizontally from the channel and exiting vertically from the bowl.

11. The method of claim 10, wherein the channel extends straight along the length, constant in thickness, and arcuately curved along the width.

12. The method of claim 10, wherein a first drift chamber is arranged to pass the flow into the neck to pass vertically up into the channel.

13. The method of claim 10, comprising:

passing the flow through at least a first change of direction prior to entering the channel; and passing the flow through at least a second change of direction, imposed by the cap upon exiting the channel.

14. The method of claim 10, comprising redirecting the flow in at least two dimensions orthogonal to one another between a first discharging, passing the flow vertically upward from the channel, and a second discharging, passing the flow vertically upward through and from the exit.

15. The method of claim 14, wherein the exit, formed in the cap is offset radially away from the tower, thereby imposing at least two changes of direction, one into a radial direction orthogonal to the length of the channel and a second in an axial direction parallel to the length of the channel.

16. The method of claim 10, comprising:

expanding a cross-sectional area (through which the flow passes) available to the flow downstream from the channel; and reducing the cross-sectional area of the flow passing through the exit.

17. The method of claim 16, comprising:

expanding, by the flow, the cross-sectional area upon atomization; and constricting the cross sectional area of the flow during passing into the channel.

18. The method of claim 17, wherein:

the bowl operates as an upper drift chamber by initially reducing and then increasing a speed of the flow between entry thereinto and exit therefrom; and the neck operates vertically above a lower drift chamber initially reducing and then increasing the speed of the flow upon entering the channel.

19. The method of claim 10, wherein:

the channel terminates at a lower (entry) end thereof with a drip edge angled to urge internally coalesced liquid, from the comparatively larger droplets separated out from the flow in the channel, to descend toward a lowest point on the drip edge;

the channel is curved along a circumferential direction with respect to a vertical (axial) axis through the bowl; and the bowl is closed at a lower end thereof, perforated only by the channel extending upward into the bowl and an aperture at the lower end, draining the bowl of externally coalesced liquid, coalesced outside the channel and inside the bowl, to a reservoir therebelow.

* * * * *